United States Patent
Tanaka (10) Patent No.: US 8,336,540 B2
(45) Date of Patent: Dec. 25, 2012

(54) PNEUMOSTOMA MANAGEMENT DEVICE AND METHOD FOR TREATMENT OF CHRONIC OBSTRUCTIVE PULMONARY DISEASE

(75) Inventor: Don Tanaka, Saratoga, CA (US)

(73) Assignee: Portaero, Inc., Cupertino, CA (US)

( * ) Notice: Subject to any disclaimer, the term of this patent is extended or adjusted under 35 U.S.C. 154(b) by 988 days.

(21) Appl. No.: 12/370,409

(22) Filed: Feb. 12, 2009

(65) Prior Publication Data
US 2009/0205641 A1    Aug. 20, 2009

Related U.S. Application Data

(60) Provisional application No. 61/029,826, filed on Feb. 19, 2008.

(51) Int. Cl.
*A61M 16/00* (2006.01)
*A61M 5/00* (2006.01)

(52) U.S. Cl. ......... 128/200.24; 128/205.27; 128/205.29; 604/45; 604/174; 604/175; 604/180; 604/304; 604/307; 604/386

(58) Field of Classification Search ............. 128/200.24, 128/200.25, 202.27, 205.12, 205.19, 205.24; 604/45, 174, 175, 180, 304, 307, 386
See application file for complete search history.

(56) References Cited

U.S. PATENT DOCUMENTS

| | | | |
|---|---|---|---|
| 733,152 A | 7/1903 | Chisholm | |
| 953,922 A | 4/1910 | Rogers | |
| 2,206,687 A | 7/1940 | Bloomheart | |
| 2,867,213 A | 1/1959 | Thomas, Jr. | |
| 2,873,742 A | 2/1959 | Shelden | |
| 2,991,787 A | 7/1961 | Shelden et al. | |
| 3,253,594 A | 5/1966 | Matthews et al. | |
| 3,384,087 A | 5/1968 | Brummelkamp | |
| 3,463,159 A | 8/1969 | Heimlich | |
| 3,511,243 A | 5/1970 | Toy | |
| 3,556,103 A | 1/1971 | Calhoun et al. | |
| 3,638,649 A | 2/1972 | Ersek | |
| 3,682,166 A | 8/1972 | Jacobs | |
| 3,688,773 A | 9/1972 | Weiss | |
| 3,777,757 A | 12/1973 | Gray et al. | |
| 3,788,326 A | 1/1974 | Jacobs | |
| 3,817,250 A | 6/1974 | Weiss et al. | |
| 3,908,704 A | 9/1975 | Clement et al. | |
| 3,916,903 A | 11/1975 | Pozzi | |
| 4,153,058 A | 5/1979 | Nehme | |

(Continued)

FOREIGN PATENT DOCUMENTS

EP    0260543 A1    3/1988

(Continued)

OTHER PUBLICATIONS

Rendina et al., "Feasibility and safety of the airway bypass procedure for patients with emphysema", The Journal of Thoracic and Cardiovascular Surgery 2003; 125: 1294-1299.

(Continued)

*Primary Examiner* — Clinton T Ostrup
(74) *Attorney, Agent, or Firm* — Fliesler Meyer LLP (57) ABSTRACT

A pneumostoma management device for maintaining the patency of a pneumostoma while controlling the flow of gases and discharge through the pneumostoma. The pneumostoma management device includes a bulb connected to a tube which enters the pneumostoma. A flow control device regulates air flow in and out of the pneumostoma via the tube. A hydrophobic filter traps discharge in the bulb while allowing gases to escape.

20 Claims, 4 Drawing Sheets

U.S. PATENT DOCUMENTS

| | | |
|---|---|---|
| 4,291,694 A | 9/1981 | Chai |
| 4,439,189 A | 3/1984 | Sargeant et al. |
| 4,465,062 A | 8/1984 | Versaggi et al. |
| 4,502,482 A | 3/1985 | DeLuccia et al. |
| 4,583,977 A | 4/1986 | Shishov et al. |
| 4,664,660 A | 5/1987 | Goldberg et al. |
| 4,799,494 A | 1/1989 | Wang |
| 4,813,929 A | 3/1989 | Semrad |
| 4,826,495 A | 5/1989 | Petersen |
| 4,828,553 A | 5/1989 | Nielsen |
| 4,869,717 A | 9/1989 | Adair |
| 4,872,869 A | 10/1989 | Johns |
| 4,889,534 A | 12/1989 | Mohiuddin et al. |
| 4,931,045 A | 6/1990 | Steer |
| 4,944,724 A | 7/1990 | Goldberg et al. |
| 4,959,054 A | 9/1990 | Heimke et al. |
| 4,976,688 A | 12/1990 | Rosenblum |
| 5,004,456 A | 4/1991 | Botterbusch et al. |
| 5,060,645 A | 10/1991 | Russell |
| 5,078,689 A | 1/1992 | Keller |
| 5,137,509 A | 8/1992 | Freitas |
| 5,139,485 A | 8/1992 | Smith et al. |
| 5,218,957 A | 6/1993 | Strickland |
| 5,230,332 A | 7/1993 | Strickland |
| 5,230,350 A | 7/1993 | Fentress |
| 5,261,708 A | 11/1993 | Steer |
| 5,263,939 A | 11/1993 | Wortrich |
| 5,312,331 A | 5/1994 | Knoepfler |
| 5,315,992 A | 5/1994 | Dalton |
| 5,336,206 A | 8/1994 | Shichman |
| 5,354,283 A | 10/1994 | Bark et al. |
| 5,356,386 A | 10/1994 | Goldberg et al. |
| 5,366,478 A | 11/1994 | Brinkerhoff et al. |
| 5,370,625 A | 12/1994 | Shichman |
| 5,376,376 A | 12/1994 | Li |
| 5,389,077 A | 2/1995 | Melinyshyn et al. |
| 5,401,262 A | 3/1995 | Karwoski et al. |
| 5,403,264 A | 4/1995 | Wohlers et al. |
| 5,431,633 A | 7/1995 | Fury |
| 5,478,333 A | 12/1995 | Asherman, Jr. |
| 5,484,401 A | 1/1996 | Rodriguez et al. |
| 5,496,297 A | 3/1996 | Olsen |
| 5,501,677 A | 3/1996 | Jensen |
| 5,501,678 A | 3/1996 | Olsen |
| 5,588,424 A | 12/1996 | Insler et al. |
| 5,616,131 A | 4/1997 | Sauer et al. |
| 5,660,175 A | 8/1997 | Dayal |
| 5,662,629 A | 9/1997 | Steer et al. |
| 5,728,066 A | 3/1998 | Daneshvar |
| 5,730,735 A | 3/1998 | Holmberg et al. |
| 5,738,661 A | 4/1998 | Larice |
| 5,807,341 A | 9/1998 | Heim |
| 5,830,200 A | 11/1998 | Steer et al. |
| 5,843,053 A | 12/1998 | Steer |
| 5,897,531 A | 4/1999 | Amirana |
| 5,931,821 A | 8/1999 | Weilbacher et al. |
| 5,954,636 A | 9/1999 | Schwartz et al. |
| 5,971,962 A | 10/1999 | Kojima et al. |
| 5,972,026 A | 10/1999 | Laufer et al. |
| 6,059,816 A | 5/2000 | Moenning |
| 6,083,255 A | 7/2000 | Laufer et al. |
| 6,174,323 B1 | 1/2001 | Biggs et al. |
| 6,197,010 B1 | 3/2001 | Leise, Jr. et al. |
| 6,200,333 B1 | 3/2001 | Laufer |
| 6,258,100 B1 | 7/2001 | Alferness et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,293,930 B1 | 9/2001 | Brunsgaard et al. |
| 6,293,951 B1 | 9/2001 | Alferness et al. |
| 6,299,633 B1 | 10/2001 | Laufer |
| 6,322,536 B1 | 11/2001 | Rosengart et al. |
| 6,328,689 B1 | 12/2001 | Gonzalez et al. |
| 6,330,882 B1 | 12/2001 | French |
| 6,334,441 B1 | 1/2002 | Zowtiak et al. |
| 6,358,269 B1 | 3/2002 | Aye |
| 6,398,775 B1 | 6/2002 | Perkins et al. |
| 6,402,754 B1 | 6/2002 | Gonzalez |
| 6,411,852 B1 | 6/2002 | Danek et al. |
| 6,416,554 B1 | 7/2002 | Alferness et al. |
| 6,432,100 B1 | 8/2002 | Affeld |
| 6,443,156 B1 | 9/2002 | Niklason et al. |
| 6,468,292 B1 | 10/2002 | Mollenauer et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,514,290 B1 | 2/2003 | Loomas |
| 6,517,519 B1 | 2/2003 | Rosen et al. |
| 6,520,183 B2 | 2/2003 | Amar |
| 6,527,761 B1 | 3/2003 | Soltesz et al. |
| 6,550,475 B1 | 4/2003 | Oldfield |
| 6,569,121 B1 | 5/2003 | Purow et al. |
| 6,569,166 B2 | 5/2003 | Gonzalez |
| 6,585,639 B1 | 7/2003 | Kotmel et al. |
| 6,589,161 B2 | 7/2003 | Corcoran |
| 6,592,594 B2 | 7/2003 | Rimbaugh et al. |
| 6,599,311 B1 | 7/2003 | Biggs et al. |
| 6,609,521 B1 | 8/2003 | Belani et al. |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,360 B1 | 10/2003 | Flodin |
| 6,634,363 B1 | 10/2003 | Danek et al. |
| 6,638,253 B2 | 10/2003 | Breznock |
| 6,653,525 B2 | 11/2003 | Ingenito et al. |
| 6,659,961 B2 | 12/2003 | Robinson |
| 6,679,264 B1 | 1/2004 | Deem et al. |
| 6,682,506 B1 | 1/2004 | Navarro |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,712,812 B2 | 3/2004 | Roschak et al. |
| 6,736,797 B1 | 5/2004 | Larsen et al. |
| 6,749,606 B2 | 6/2004 | Keast et al. |
| 6,770,063 B2 | 8/2004 | Goldberg et al. |
| 6,770,070 B1 | 8/2004 | Balbierz |
| 6,790,172 B2 | 9/2004 | Alferness et al. |
| 6,827,086 B2 | 12/2004 | Shuman |
| 6,837,906 B2 | 1/2005 | Ginn |
| 6,840,243 B2 | 1/2005 | Deem et al. |
| 6,843,767 B2 | 1/2005 | Corcoran et al. |
| 6,846,292 B2 | 1/2005 | Bakry |
| 6,849,061 B2 | 2/2005 | Wagner |
| 6,852,108 B2 | 2/2005 | Barry et al. |
| 6,860,847 B2 | 3/2005 | Alferness et al. |
| 6,878,141 B1 | 4/2005 | Perkins et al. |
| 6,886,558 B2 | 5/2005 | Tanaka |
| 6,901,927 B2 | 6/2005 | Deem et al. |
| 6,904,909 B2 | 6/2005 | Andreas et al. |
| 6,905,518 B2 | 6/2005 | Ginn |
| 6,916,310 B2 | 7/2005 | Sommerich |
| 6,929,637 B2 | 8/2005 | Gonzalez et al. |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |

| | | |
|---|---|---|
| 7,252,086 B2 | 8/2007 | Tanaka |
| 7,377,278 B2 | 5/2008 | Tanaka |
| 7,398,782 B2 | 7/2008 | Tanaka |
| 7,406,963 B2 | 8/2008 | Chang et al. |
| 7,426,929 B2 | 9/2008 | Tanaka |
| 7,533,667 B2 | 5/2009 | Tanaka |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0120177 A1 | 8/2002 | Borst et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0087831 A1 | 5/2004 | Michels et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0199128 A1 | 10/2004 | Morris et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle, Jr. |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |
| 2006/0079838 A1 | 4/2006 | Walker et al. |
| 2006/0095002 A1 | 5/2006 | Soltesz et al. |
| 2006/0107961 A1 | 5/2006 | Tanaka |
| 2006/0116749 A1 | 6/2006 | Willink et al. |
| 2006/0118125 A1 | 6/2006 | Tanaka |
| 2006/0118126 A1 | 6/2006 | Tanaka |
| 2006/0124126 A1 | 6/2006 | Tanaka |
| 2006/0130830 A1 | 6/2006 | Barry |
| 2006/0135947 A1 | 6/2006 | Soltesz et al. |
| 2006/0135984 A1 | 6/2006 | Kramer et al. |
| 2006/0142672 A1 | 6/2006 | Keast et al. |
| 2006/0161233 A1 | 7/2006 | Barry et al. |
| 2006/0162731 A1 | 7/2006 | Wondka et al. |
| 2006/0206147 A1 | 9/2006 | DeVore et al. |
| 2006/0212046 A1 | 9/2006 | Pearce et al. |
| 2006/0212051 A1 | 9/2006 | Snyder et al. |
| 2006/0235432 A1 | 10/2006 | DeVore et al. |
| 2006/0235467 A1 | 10/2006 | DeVore |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2007/0005083 A1 | 1/2007 | Sabanathan et al. |
| 2007/0027434 A1 | 2/2007 | Pedersen et al. |
| 2007/0043350 A1 | 2/2007 | Soltesz et al. |

| | | | |
|---|---|---|---|
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |
| 2007/0299424 A1 | 12/2007 | Cumming et al. | |
| 2008/0281151 A1 | 11/2008 | Chang et al. | |
| 2008/0281295 A1 | 11/2008 | Chang et al. | |
| 2008/0281433 A1 | 11/2008 | Chang et al. | |
| 2008/0283065 A1 | 11/2008 | Chang et al. | |
| 2008/0287878 A1 | 11/2008 | Tanaka | |
| 2008/0287973 A1 | 11/2008 | Aster et al. | |
| 2008/0295829 A1 | 12/2008 | Evens | |
| 2009/0205641 A1 | 8/2009 | Tanaka | |
| 2009/0205643 A1 | 8/2009 | Tanaka et al. | |
| 2009/0205644 A1 | 8/2009 | Tanaka et al. | |
| 2009/0205645 A1 | 8/2009 | Tanaka et al. | |
| 2009/0205646 A1 | 8/2009 | Tanaka et al. | |
| 2009/0205647 A1 | 8/2009 | Plough et al. | |
| 2009/0205648 A1 | 8/2009 | Tanaka et al. | |
| 2009/0205649 A1 | 8/2009 | Tanaka et al. | |
| 2009/0205650 A1 | 8/2009 | Tanaka et al. | |
| 2009/0205651 A1 | 8/2009 | Tanaka et al. | |
| 2009/0205658 A1 | 8/2009 | Tanaka et al. | |
| 2009/0205665 A1 | 8/2009 | Tanaka et al. | |
| 2009/0209856 A1 | 8/2009 | Tanaka et al. | |
| 2009/0209906 A1 | 8/2009 | Tanaka et al. | |
| 2009/0209909 A1 | 8/2009 | Tanaka et al. | |
| 2009/0209917 A1 | 8/2009 | Tanaka et al. | |
| 2009/0209924 A1 | 8/2009 | Tanaka | |
| 2009/0209936 A1 | 8/2009 | Tanaka et al. | |
| 2009/0209970 A1 | 8/2009 | Tanaka et al. | |
| 2009/0209971 A1 | 8/2009 | Tanaka et al. | |

FOREIGN PATENT DOCUMENTS

| | | | |
|---|---|---|---|
| JP | 62-2028747 U | | 6/1986 |
| RU | 2192185 | | 10/2002 |
| WO | WO 96/39960 | | 12/1996 |
| WO | WO 99/66975 | | 12/1999 |
| WO | WO 00/76577 | A1 | 12/2000 |
| WO | WO 01/45568 | A1 | 6/2001 |

OTHER PUBLICATIONS

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&Ing=e...> May 2, 2007.

Shah, Pallav, "Surgical and Non-surgical Volume Reduction for COPD", Presented at the Clinical Consensus on COPD, Mar. 2-3, 2007, Novotel London West, pp. 1-44.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prosteses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woodring et al., "Pneumothorax ex vacuo", Chest 1996, 110: 1102-1124.

Woolcock et al., "Mechanical factors influencing collateral ventilation in human, dog, and pig lungs", Journal of Applied Physiology 1971, 30: 99-115.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

International Search Report for PCT/US/2009/034374 dated Aug. 28, 2009; 13 pages.

International Search Report for PCT/US/2009/034380 dated Sep. 24, 2009; 12 pages.

International Search Report for PCT/US2009/034322 dated Oct. 5, 2009; 14 pages.

International Search Report for PCT/US2009/034406 dated Dec. 2, 2009; 16 pages.

Aljuri et al., "Validation and pilot clinical study of a new bronchoscopic method to measure collateral ventilation before endobronchial lung volume reduction", J Appl Physio 106: 774-783, 2009.

Al-Salem et al., "Computed tomography-guided percutaneous needle aspiration of lung abscesses in neonates and children", Pediatr Surg Int (1997) 12: 417-419, copyright Springer-Verlag 1997.

Ball, Jr et al., "Percutaneous Drainage of Chest Abscesses in Children", Radiology 1989; 171: 431-434.

Becker et al., "Lung Volumes before and after Lung Volume Reduction Surgery: Quantitative CT Analysis", Am J Respir Crit Care Med 1998; 157: 1593-1599.

Brenner et al., "Innovative Approaches to Lung Volume Reduction for Emphysema", Chest 2004; 126: 238-248.

Brutinel et al., "A two-year experience with the neodymium-YAG laser in endobronchial obstruction", Chest 1987; 91: 159-165.

Celli et al. "Standards for the diagnosis and treatment of patients with COPD: a summary of the ATS/ERS position paper", European Respiratory Journal 2004; 23; 932-946.

Cetti et al., "Collateral ventilation", Thorax 2006; 61: 371-373.

Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System, (2003).

Choong et al., "Feasibility and safety of airway bypass stent placement and influence of topical mitomycin C on stent patency", The Journal of Thoracic and Cardiovascular Surgery 2005; 129: 632-638.

Choong et al., "Transpleural ventilation of explanted human lungs", Thorax 2007; 62: 623-630; originally published online Apr. 5, 2007.

Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.

Dumon, J. F., "A Dedicated Tracheobronchial Stent", Chest 1990; 97: 328-332.

Eloesser, "An Operation for Tuberculous Empyema", Chest 1935; 1: 8-23.

Fein, Alan M, "Lung Volume Reduction Surgery: Answering the Crucial Questions", Chest 1998; 113: 277-282.

Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.

Fessler, Henry E., "Collateral Ventilation, the Bane of Bronchoscopic Volume Reduction", Am J Respir Crit Care Med 2005; 171: 423-425.

Frawley et al., "Airway Pressure Release Ventilation: Theory and Practice", AACN Clinical Issues 2001; vol. 12, No. 2: 234-246.

Freitag et al., "Theoretical and experimental basis for the development of a dynamic airway stent", European Respiratory Journal 1994; 7: 2038-2045.

Ghaye et al., "Imaging guided thoracic interventions", European Respiratory Journal 2001; 17: 507-528.

Golding et al., "External drainage of large bullae in severe generalized emphysema", Journal of Thoracic and Cardiovascular Surgery Jun. 1968; vol. 55, No. 6: 891-894.

Goldstraw et al., "The Surgical Treatment of Emphysema: The Brompton Approach", Chest Surgery Clinics of North America Nov. 1995; vol. 5, No. 4: 777-797.

Habashi, Nader M., "Other approaches to open-lung ventilation: Airway pressure release ventilation", Crit Care Med 2005, vol. 33, No. 3 (Suppl): S228-S240.

Harada et al., "Re-expansion of Refractory Atelectasis Using a Bronchofiberscope with a Balloon Cuff", Chest 1983; 84: 725-728.

Head et al., "Intracavitary Suction (Monaldi) in the Treatment of Emphysematous Bullae and Blebs", Journal of Thoracic Surgery Dec. 1949; vol. 18, No. 6: 761-776.

Heimlich, Henry J., "Respiratory Rehabilitation with Transtracheal Oxygen System", Ann Otol Rhinol Laryngol Nov./Dec. 1982; 91: 643-647.

Hogg et al., "Chronic obstructive pulmonary disease c2: Pathology and biochemistry of emphysema", Thorax 2002; 57: 830-834.

Hogg et al., "The Resistance of Collateral Channels in Excised Human Lungs", Journal of Clinical Investigation 1969; 48: 421-431.

Joannette, Albert, "Drainage of Tuberculous Cavities by Aspiration (Monaldi Method)", The Canadian Medical Association Journal Jan. 1941; 46-48.

Korpela et al., "Bioabsorbable Self-reinforced Poly-L-Lactide, Metallic, and Silicone Stents in the Management of Experimental Tracheal Stenosis", Chest 1999; 115: 490-495.

Lausberg et al., "Bronchial Fenestration Improves Expiratory Flow in Emphysematous Human Lungs", Annals of Thoracic Surgery 2003; 75: 393-398.

Lorenzo et al., "Lung Abscesses in Children: Diagnostic and Therapeutic Needle Aspiration", Radiology Oct. 1985; 157: 79-80.

MacArthur et al., "Intracavity suction and drainage in the treatment of emphysematous bullae", Thorax 1977; 32: 668-672.

MacKlem, Peter T., "Collateral Ventilation", The New England Journal of Medicine Jan. 5, 1978; 298(1): 49-50.

Matson et al., "Evaluation of Various Surgical Procedures in the Treatment of Pulmonary Tuberculosis", Chest 1946; 12: 40-47.

McCoy, Robert, "Oxygen-Conserving Techniques and Devices", Respiratory Care Jan. 2000, vol. 45, No. 1: 95-104.

Meyers et al., "Chronic obstructive pulmonary disease 10: Bullectomy, lung volume reduction surgery, and transplantation for patients with chronic obstructive pulmonary disease", Thorax 2003; 58: 634-638.

Mineo et al., "Awake Nonresectional Lung Volume Reduction Surgery", Annals of Surgery 2006; 243: 131-136.

Monaldi, V., "Endocavitary Aspiration: Its Practical Application", Tubercle 1947: 223-228.

Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

U.S. Department of Health and Human Services; National Institutes of Health National Heart, Lung, and Blood Institute; "Chronic Obstructive Pulmonary Disease", NIH Publication No. 03-5229 Mar. 2003: 1-6.

Parker et al., "Percutaneous small bore catheter drainage in the management of lung abscesses", Chest 1987; 92: 213-218.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction", European Respiratory Review 2006; 15(100): 99-103.

PNEUMOSTOMA MANAGEMENT DEVICE AND METHOD FOR TREATMENT OF CHRONIC OBSTRUCTIVE PULMONARY DISEASE

CLAIM TO PRIORITY

This application claims priority to U.S. Provisional Patent Application No. 61/029,836 filed Feb. 19, 2008 entitled "PNEUMOSTOMA MANAGEMENT DEVICE AND METHOD FOR TREATMENT OF CHRONIC OBSTRUCTIVE PULMONARY DISEASE" which is incorporated herein by reference.

BACKGROUND OF THE INVENTION

In the United States alone, approximately 14 million people suffer from some form of chronic obstructive pulmonary disease. However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion (FIG. 11). COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments, for ameliorating the symptoms. The goal of current treatments is to help people live with the disease more comfortably and to prevent the progression of the disease. The current options include: self-care (e.g., quitting smoking), medications (such as bronchodilators which do not address emphysema physiology), long-term oxygen therapy, and surgery (lung transplantation and lung volume reduction surgery). Lung volume reduction surgery is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and have unproven efficacy. None of the surgical approaches to treatment of COPD has been widely adopted. Therefore, a large unmet need remains for a medical procedure that can sufficiently alleviate the debilitating effects of COPD and emphysema.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a pleurodesis between the visceral and parietal membranes surrounding the passageway as it enters the lung. The pleurodesis prevents air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The artificial aperture into the lung through the chest is referred to herein as a pneumostoma. The pneumostoma provides an extra pathway that allows air to exit the lungs while bypassing the natural airways which have been impaired by COPD and emphysema. By providing this ventilation bypass, the pneumostoma allows the stale air trapped in the lung to escape from the lung. By shrinking the lung, the ventilation bypass allows more fresh air to be drawn in through the natural airway and increases the effectiveness of all of the tissues of the lung. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing a portion of the lung or sealing off a portion of the lung.

In accordance with an embodiment of the present invention a partially-implantable pneumostoma management device is provided which can be placed into a pneumostoma to prevent the entry of foreign substances into the lung, control air flow through the pneumostoma and collect any materials that may exit the lung.

In accordance with another embodiment of the present invention a pneumostoma management device is provided with a hydrophobic filter element. The pneumostoma management device includes a hydrophobic filter to prevent the entry of water into the device and pneumostoma.

In accordance with another embodiment of the present invention a pneumostoma management device is provided with a flow-control device. The flow-control device permits air to flow out of the pneumostoma but inhibits the flow of air into the pneumostoma.

In accordance with another embodiment of the present invention a pneumostoma management device is provided with an integral trap chamber. The integral trap system for collecting any liquid or particulate matter which may be emitted through the pneumostoma.

In accordance with another embodiment of the present invention a method for controlling entry and exit of material through a pneumostoma is provided in which the disclosed pneumostoma management device is temporarily implanted in a pneumostoma.

In accordance with a particular embodiment of the present invention, a pneumostoma management device is configured to be mounted on a chest of a patient to treat a lung of a patient and control the flow of liquids and gases through a pneumostoma. The pneumostoma management device includes a tube adapted to pass into the pneumostoma wherein the tube has a distal opening adapted to be positioned within the lung to allow liquids and gases to enter the tube from the lung. The pneumostoma management device also includes a bulb connected to a proximal end of the tube wherein the bulb defines a chamber. A one-way valve is positioned between the distal opening of the tube and the chamber such that liquids and gases may enter the chamber from the tube but are prevented from leaving the chamber through the one-way valve. The bulb has an external opening in which a hydrophobic filter is positioned which allows gases to escape the chamber via the external opening but prevents liquids from escaping the chamber via the external opening. The pneumostoma management device thus allows gases to pass from the lung of the patient through the pneumostoma management device and escape through the external aperture. Whereas liquids pass from the lung into the chamber where they are trapped between the one-way valve and the hydrophobic filter.

Thus, various devices and methods are provided for managing a pneumostoma. Other objects, features and advantages of the invention will be apparent from drawings and detailed description to follow.

BRIEF DESCRIPTION OF THE DRAWINGS

The above and further features, advantages and benefits of the present invention will be apparent upon consideration of the present description taken in conjunction with the accompanying drawings.

DETAILED DESCRIPTION OF THE INVENTION

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Pneumostoma Formation and Anatomy

Figure 1A:
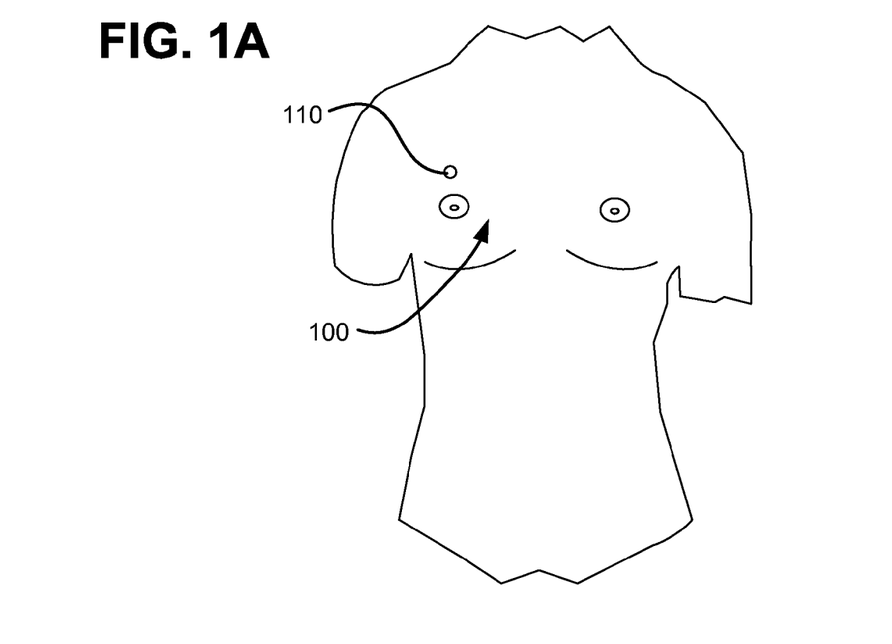
FIG. 1A shows the chest of a patient showing a pneumostoma that may be managed using the device and methods of the present invention.

FIG. 1A shows the chest of a patient showing a pneumostoma that may be managed using the device and methods of the present invention. Pneumostoma 110 is shown on the front of the chest 10 over the right lung (not shown). In general one pneumostoma per lung is created however, more or less than one pneumostoma per lung may be created depending upon the needs of the patient. A pneumostoma is surgically created by forming an artificial channel through the chest wall and joining that channel with an opening through the visceral membrane of the lung into parenchymal tissue of the lung to form an anastomosis. The anastomosis is preferably joined and sealed by sealing the channel to the lung using adhesions such as a pleurodesis. Methods for forming the channel, opening, anastomosis and pleurodesis or the pneumostoma are disclosed in applicant's commonly-owned, patents and patent applications including U.S. patent application Ser. No. 10/881,408, now U.S. Pat. No. 7,682,332, issued Mar. 23, 2010, entitled "Methods and Devices to Accelerate Wound Healing in Thoracic Anastomosis Applications" and U.S. Provisional Patent Application Ser. No. 60/938,466 entitled "Variable Parietal/Visceral Pleural Coupling" which are incorporated herein by reference.

Figure 1B:
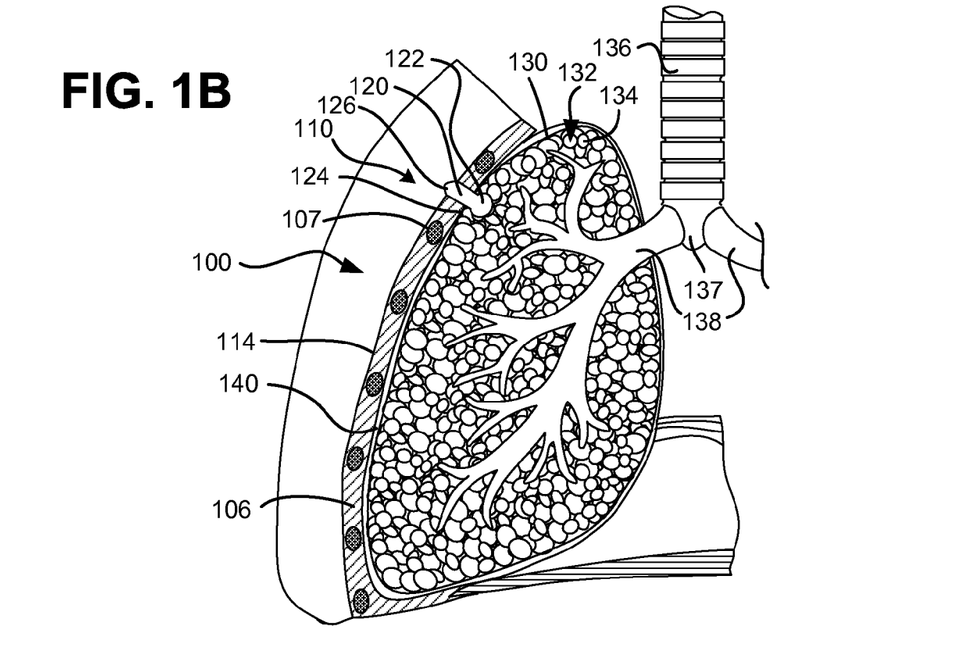
FIG. 1B shows a sectional view of the chest illustrating the relationship between the pneumostoma, lung and natural airways.

FIG. 1B shows a sectional view of the chest 100 illustrating the position of the pneumostoma 110. The parenchymal tissue of the lung is comprised principally of alveoli 134. The alveoli 134 are the thin walled air-filled sacs in which gas exchange takes place. Air flows into the lungs through the natural airways including the trachea 136, carina 137, and bronchi 138. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel 120 through the thoracic wall 106 of the chest 100 between the ribs 107. Channel 120 opens at an aperture 126 through the skin 114 of chest 100. The channel 120 is joined to a cavity 122 within the parenchymal tissue 132 of lung 130.

Figure 1C:
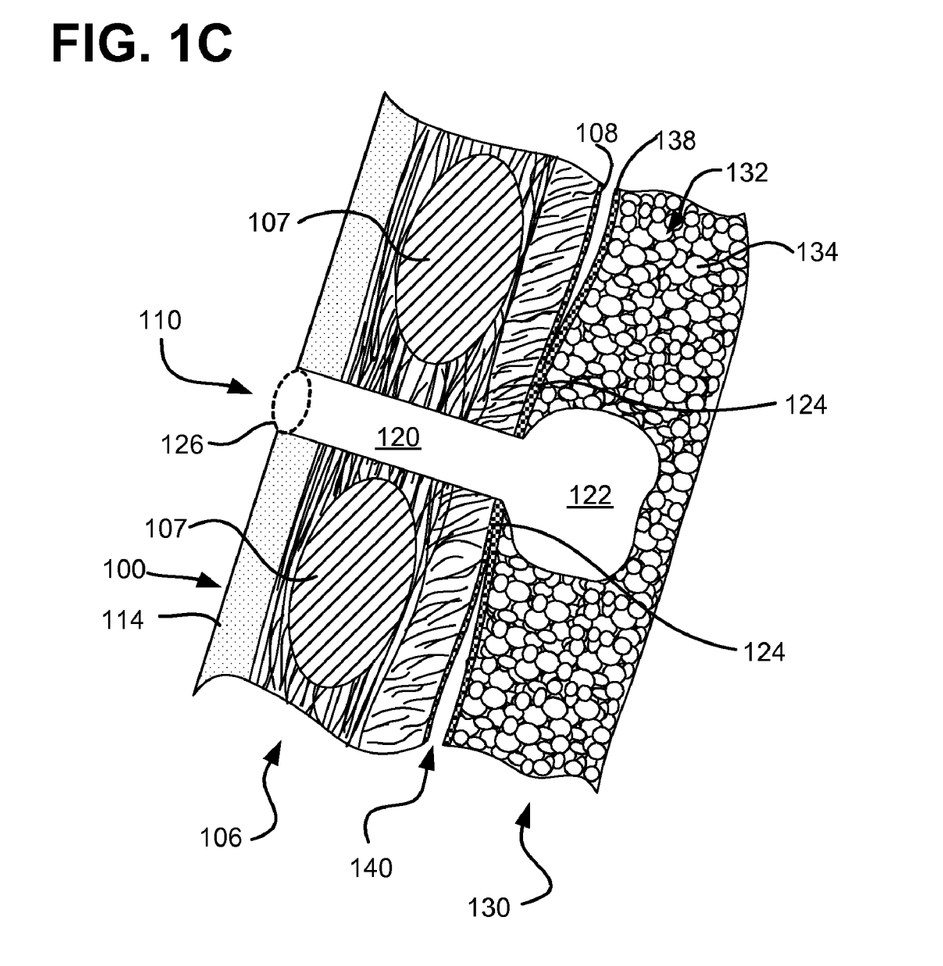
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124 the pleural membranes are fused and/or adhered to one another eliminating the space between the pleural membranes in that region.

An important feature of the pneumostoma is the adhesion or pleurodesis 124 surrounding the channel 120 where it enters the lung 130. The pleurodesis 124 is the localized fusion or adhesion of the parietal membrane 108 and visceral membrane 138. The pleurodesis 124 surrounding the channel 120 prevents air from the lung 130 or channel 120 from entering the pleural cavity 140. If air is permitted to enter pleural cavity 140, a pneumothorax would result and the lung would collapse. One method for creating pleurodesis between the visceral pleura of the lung and the inner wall of the thoracic cavity uses chemical methods, including irritants such as Doxycycline and/or Bleomycin, surgical methods, including pleurectomy or thoracoscopic talc pleurodesis, or radiotherapy methods, including radioactive gold or external radiation. All of these methods inflames and fuse the pleural membranes. Alternatively adhesion can be created between the pleural membranes using biocompatible glues. A range of biocompatible glues are available that may be used on the lung, including light-activatable glues, fibrin glues, and two part polymerizing glues.

The pneumostoma 110 provides an extra pathway for exhaled air to exit the lung 130 without passing through the major natural airways such as the bronchi 138 and trachea 136. Collateral ventilation is the term given to leakage of air through the connective tissue between the alveoli 134. This air typically becomes trapped in the lung and contributes to hyperinflation. Collateral ventilation is particularly prevalent in an emphysemous lung because of the deterioration of lung tissue caused by COPD. In lungs that have been damaged by COPD and emphysema the resistance to flow in collateral channels (not shown) of the parenchymal tissue 132 is reduced allowing collateral ventilation to increase. By providing pneumostoma 110, air from alveoli 134 of parenchymal tissue 132 that passes into collateral pathways of lung 130 is collected in cavity 122 of pneumostoma 110. Pneumostoma 110 thus makes use of collateral ventilation to collect air in cavity 122 of pneumostoma 110 and vent the air outside the body while bypassing the natural airways which have been impaired by COPD and emphysema.

By providing this ventilation bypass, the pneumostoma allows the stale air trapped in the parenchymal tissue 132 to escape from the lung 130 and reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. The pneumostoma not only provides an extra pathway that allows air to exit the lungs but also allows more fresh air to be drawn in through the natural airway and increases the effectiveness of all of the tissues of the lung improving gas exchange. The pneumostoma thus achieves many of the advantages sought by lung volume reduction surgery without surgically removing a portion of the lung or sealing off a portion of the lung.

Applicants have found that a pneumostoma management device in accordance with embodiments of the present invention is desirable to prevent the entry of foreign matter into lung 130.

Pneumostoma Management Device

Figure 2A:
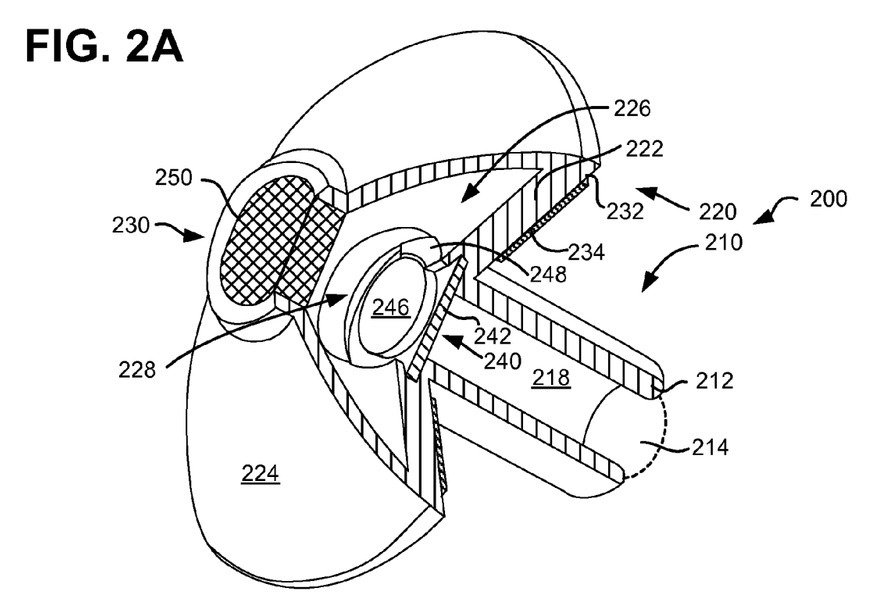
FIG. 2A shows a perspective cutaway view of a pneumostoma management device according to an embodiment of the present invention.
Figure 2B:
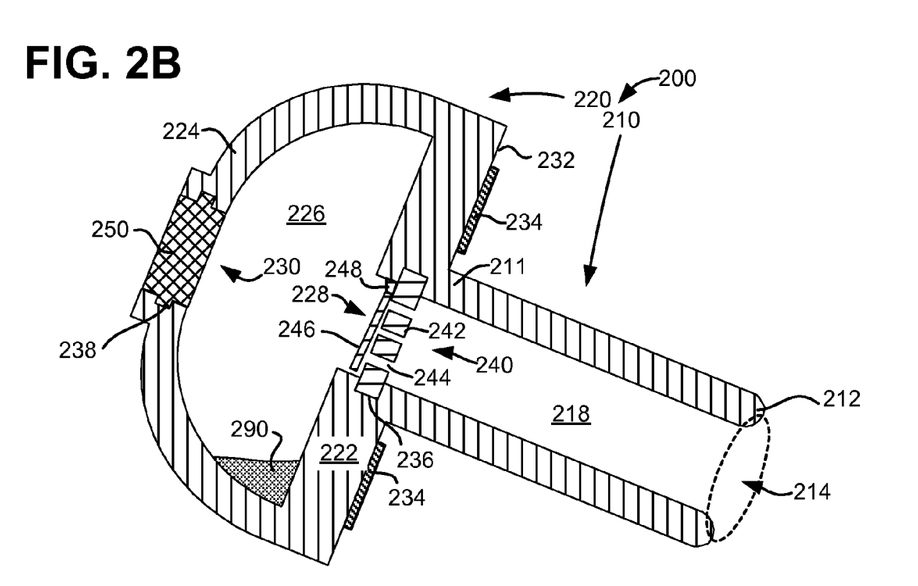
FIG. 2B shows a sectional view of a pneumostoma management device according to an embodiment of the present invention.

FIGS. 2A and 2B illustrate a pneumostoma management device ("PMD") 200 in accordance with an embodiment of the present invention. PMD 200 comprises an implantable sleeve 210 joined at its proximal end 211 with a bulb 220 which may be mounted to the skin of the patient. In a preferred embodiment sleeve 210 is formed in one piece with bulb 220. In preferred embodiments, sleeve 210 and bulb 220 are formed from biocompatible polymers or a biocompatible metal, for example, stainless steel.

Sleeve 210 preferably comprises a rounded distal tip 212 as shown in FIGS. 2A and 2B. Tip 212 in order to reduce irritation of damage to the tissues of the pneumostoma or lung during insertion or while in position. Sleeve 210 has an opening 214 in tip 212. Opening 214 allows the entry of gases from the cavity of the pneumostoma into sleeve 210 and thence via the lumen 218 of sleeve 210 to the bulb 220.

Bulb 220 is connected to the proximal end 211 of sleeve 210. In one embodiment, illustrated in FIGS. 2A and 2B, bulb 220 comprises a flange 222 and a dome 224. The flange 222 and dome 224 define a chamber 226. The chamber 226 has an entrance aperture 228 and at least one exit aperture 230. Exhaled air and solid material may flow from lumen 218 of sleeve 210 into chamber 226 through entrance aperture 228. Exhaled air may exit chamber 226 through exit aperture 240 to vent to atmosphere outside of the patient's body.

For simplicity of manufacturing, flange 222, and dome 224 may be formed in one piece as shown in FIG. 2B. Bulb 220 has a smooth surface and a low profile so it is comfortable for the patient to wear. Bulb 220 is designed so as not to snag on the patient's clothing or to restrict motion of the patient. Chamber 226 is sized and configured to receive liquid and/or solid material 290 such as mucous which may be exhaled from the lung through the pneumostoma 110.

Flange 222 is significantly wider than sleeve 210. Flange 222 thus comprises a contact surface 232 perpendicular to sleeve 210 and surrounding sleeve 210 which, when the sleeve 210 of PMD 200 is positioned in a pneumostoma 110, will contact the skin of the patient surrounding pneumostoma 110. The contact surface 232 serves as an insertion limit to prevent over-insertion of sleeve 210 into a pneumostoma 110. Flange 222 is designed such that it sufficiently flexible that it can conform to the skin 114 of chest 100. Contact surface 232 is also provided with a biocompatible adhesive 234, such as a hydrocolloid adhesive, for securing PMD 200 to the skin 114 of the patient. Adhesive 234 should be selected so as to help maintain the correct position of PMD 200 without causing undue irritation to the skin of the patient.

A flow control device 240 is positioned in aperture 228 between lumen 218 of sleeve 210 and chamber 226. Flow control device 240 is positioned and mounted such that material moving between lumen 218 and chamber 226 must pass through flow control device 240. In the embodiment shown in FIGS. 2A and 2B, flange 222 is provided with a recess 236 into which flow control device 240 may be mounted.

Flow control device 240 may comprise a one-way valve assembly such as a flapper valve, Heimlich valve, reed valve, or the like, for allowing air to be exhaled through entrance aperture 228 into chamber 226 while restricting the flow of air or other matter into lumen 218 from chamber 226. It is desirable to restrict flow of air in through the pneumostoma so as to encourage a reduction in hyperinflation and to prevent the inhalation of solid or liquid matter from into the lung through the pneumostoma. The flow control device 240 shown in FIG. 2B comprises a fixed disc 242 having a number of apertures 244. Above fixed disc 242 is a flapper disc 246. Flapper disc 246 is kept in place above fixed disc 242 by hinge 248. When the air pressure in lumen 218 is greater than the air pressure in chamber 226 during exhalation, flapper disc 246 moves away from fixed disc 242 and air may pass through a space between fixed disc 242 and flapper disc 246 and enter chamber 226 from lumen 218. However, when the air pressure in lumen 218 is less than the air pressure in chamber 226 during inhalation, flapper disc 246 moves towards fixed disc 242 and obstructs the apertures 244 in fixed disc 242 such that no air may pass into lumen 218 from chamber 226.

A hydrophobic filter 250 is positioned in exit aperture 230 between chamber 226 and the exterior of bulb 220. Hydrophobic filter 250 is positioned and mounted such that material moving between chamber 226 and the exterior of bulb 220 must pass through hydrophobic filter 250. Hydrophobic filter 250 prevents the flow of water in and out of chamber 226 through exit aperture 230. In the embodiment shown in FIGS. 2A and 2B, bulb 224 is provided with a recess 238 into which hydrophobic filter 250 may be press fit.

Use of the Pneumostoma Management Device

Figure 3A:
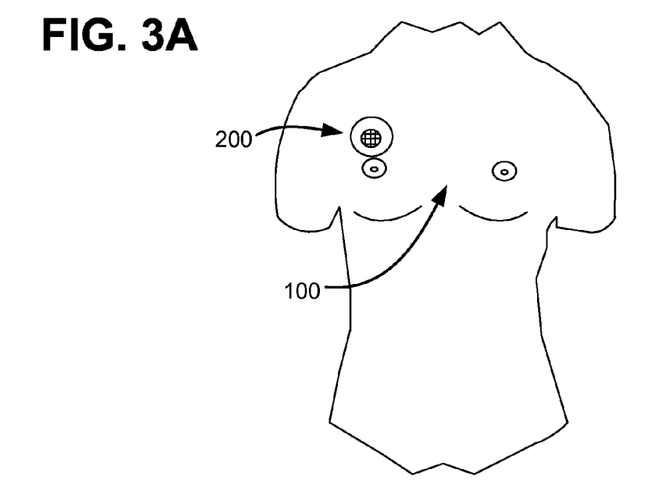
FIG. 3A shows the chest of a patient illustrating placement of the pneumostoma management device according to an embodiment of the present invention.

FIG. 3A illustrates the use of PMD 200 in pneumostoma 110 of FIG. 1A. As shown in FIG. 3A the low profile of PMD 200 allows it to be inconspicuously positioned on the chest 100 of a patient in the frontal 110 location. PMD 200 is designed so as not to interfere with the range or motion or clothing of the patient. This is of importance for a device such as PMD 200 which must be used continuously to be effective. Comfort and ease of use are important if patient compliance with treatment protocols is to be achieved.

Figure 3B:
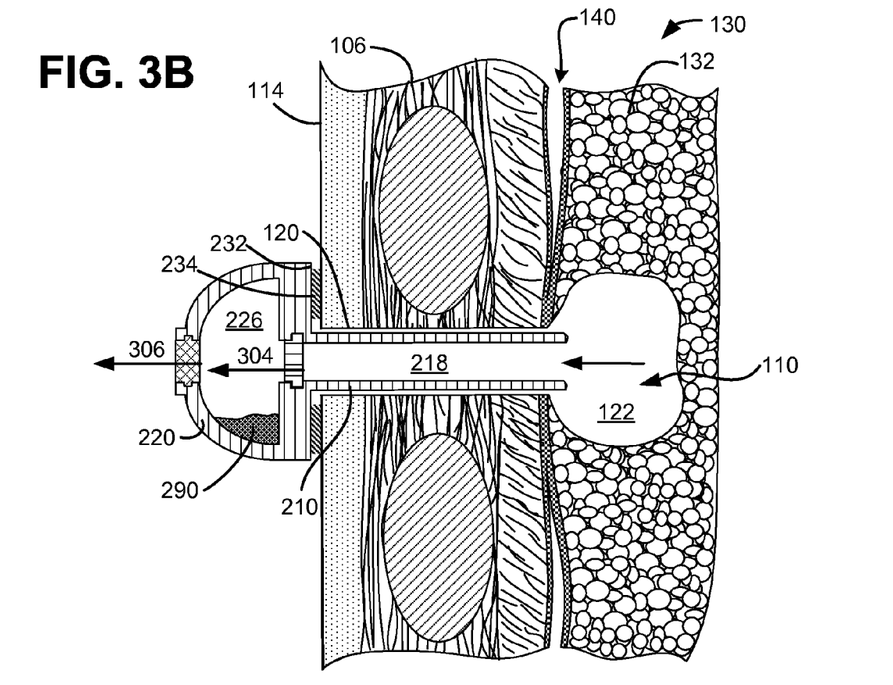
FIG. 3B shows a sectional view of a pneumostoma illustrating placement of the pneumostoma management device according to an embodiment of the present invention.

FIG. 3B shows a sectional view through PMD 200 and pneumostoma 110 showing the interaction of the PMD with the pneumostoma 110. It should be noted that sleeve 210 fits snugly within channel 120 of pneumostoma 110. Sleeve 210 is sized and configured such that it penetrates through channel 120 into cavity 122 in the parenchymal tissue 132 of lung 130. Contact surface 232 of flange 222 is pushed into contact with skin 114 of the thoracic wall 106 of chest 100 thus preventing further insertion of sleeve 210. Adhesive 234 contacts skin 114 holding PMD 200 in position. Flange 222 conforms to the surface of chest 100 to secure PMD 200 to chest 100 with adhesive 234.

Because of the snug fit of sleeve 210 within channel 120 and the contact between flange 222 and/or adhesive 234 with skin 114, PMD 200 effectively controls the movement of all material in or out of the pneumostoma. From lumen 218, exhaled air flows through flow control device 240 into chamber 226 as shown by arrow 304. Any liquid and/or solid material 290 remains trapped in chamber 226. Air flows out of chamber 226 to the exterior of PMD 200 and the patient through hydrophobic filter 250 as shown by arrow 306. Thus PMD 200 allows air to exit pneumostoma 110 and vent to atmosphere while preventing the entry of water or solids into the pneumostoma 110.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A pneumostoma management device adapted to be mounted on a chest of a patient to treat a lung of a patient and control flow of liquids and gases through a pneumostoma wherein the pneumostoma management device comprises:
    a tube adapted to pass into the pneumostoma wherein the tube has a distal opening adapted to be positioned within the lung to allow liquids and gases to enter the tube from the lung;
    a bulb connected to a proximal end of the tube wherein the bulb defines a chamber;
    a one-way valve positioned between the distal opening of the tube and the chamber such that liquids and gases may enter the chamber from the tube and are prevented from leaving the chamber through the one-way valve;
    an external opening in the bulb;
    a hydrophobic filter positioned in the external opening which allows gases to escape the chamber via the external opening and which prevents liquids from escaping the chamber via the external opening;
    whereby gases may pass from the lung of the patient through the pneumostoma management device and escape through the external aperture and whereby liquids may pass from the lung into the chamber where they are trapped between the one-way valve and the hydrophobic filter.

2. The pneumostoma management device of claim 1, wherein the bulb comprises a flange substantially perpendicular to the tube and adapted to contact the chest of the patient surrounding the pneumostoma to prevent over-insertion of the tube.

3. The pneumostoma management device of claim 2, wherein the flange comprises an adhesive positioned to secure the flange to the chest of the patient.

4. The pneumostoma management device of claim 2, wherein the flange comprises a hydrocolloid adhesive positioned to secure the flange to the chest of the patient.

5. The pneumostoma management device of claim 1, wherein the flange is adapted to conform to the chest of the patient.

6. The pneumostoma management device of claim 1, wherein the one-way valve is press-fit into the bulb where the tube connects to the bulb.

7. The pneumostoma management device of claim 1, wherein the one-way valve comprises one of a reed valve, a flapper valve and a Heimlich valve.

8. The pneumostoma management device of claim 1, wherein the bulb is formed in one piece with the tube.

9. The pneumostoma management device of claim 1, wherein the hydrophobic filter is press-fit into the external opening of the bulb.

10. A medical device adapted to control movement of gases and non-gaseous discharge through a pneumostoma wherein the medical device comprises:
    a tube adapted to pass into the pneumostoma wherein the tube has a distal opening adapted to be positioned within the lung to allow gases and non-gaseous discharge to enter the tube from the lung;
    a bulb connected to a proximal end of the tube wherein the bulb defines a chamber adapted to contain the non-gaseous discharge;
    a valve configured such that gases and non-gaseous discharge may enter the chamber from the tube and are prevented from leaving the chamber through the tube;
    an external opening in the bulb;
    a filter positioned in the external opening which allows gases to escape the chamber via the external opening and which prevents non-gaseous discharge from escaping the chamber via the external opening;

whereby gases may escape for the lung through the medical device and discharge is trapped in the chamber between the valve and the filter.

11. The medical device of claim 10, wherein the bulb comprises a contact surface substantially perpendicular to the tube and adapted to contact a chest of a patient to limit insertion of the tube into the pneumostoma.

12. The medical device of claim 10, wherein the bulb comprises a contact surface substantially perpendicular to the tube and bearing an adhesive adapted to temporarily secure the bulb to a chest of a patient.

13. The medical device of claim 10, wherein the bulb comprises a contact surface substantially perpendicular to the tube and bearing a hydrocolloid adhesive adapted to releasably secure the bulb to a chest of a patient.

14. The medical device of claim 13, wherein the contact surface is sufficiently flexible to conform to the chest of the patient.

15. The medical device of claim 10, wherein the valve comprises a valve selected from a one-way valve, a reed valve, a flapper valve and a Heimlich valve.

16. The medical device of claim 10, wherein the valve fits in a recess in the flange.

17. The medical device of claim 10, wherein the hydrophobic filter fits in a recess in the bulb.

18. The medical device of claim 10, wherein the bulb and tube are formed in one piece.

19. A medical device adapted to control movement of gases and non-gaseous discharge through a pneumostoma wherein the medical device comprises:

a tube formed in one piece with a bulb wherein the bulb comprises a contact surface substantially larger in diameter than the tube and wherein the tube extends substantially perpendicular to the contact surface such that the tube is adapted to be pushed into the pneumostoma until the contact surface contacts a chest of a patient;

a chamber within the bulb connected to a lumen which passes through the tube to an opening in a distal end of the tube;

a valve configured to allow gases and non-gaseous discharge to enter the chamber from the lumen and prevent gases and non-gaseous discharge from leaving the chamber through the lumen;

an external opening in the bulb;

a filter positioned in the external opening which allows gases to escape the chamber via the external opening and which prevents non-gaseous discharge from escaping the chamber via the external opening;

whereby the medical device controls movement of gases and non-gaseous discharge through the pneumostoma.

20. The medical device of claim 19, wherein the contact surface includes a biocompatible adhesive adapted to releasably secure the bulb to the chest of the patient.

* * * * *

UNITED STATES PATENT AND TRADEMARK OFFICE
CERTIFICATE OF CORRECTION

PATENT NO. : 8,336,540 B2
APPLICATION NO. : 12/370409
DATED : December 25, 2012
INVENTOR(S) : Don Tanaka It is certified that error appears in the above-identified patent and that said Letters Patent is hereby corrected as shown below:

Col. 1, line 9, after "Application No." delete "61/029,836"; insert --61/029,826--

Signed and Sealed this
Twenty-ninth Day of January, 2013

David J. Kappos
*Director of the United States Patent and Trademark Office*